United States Patent [19]

Jurisch

[11] 3,994,919
[45] Nov. 30, 1976

[54] VINYL OXAZOLIDINES

[75] Inventor: Louis A. Jurisch, Marengo, Ill.

[73] Assignee: IMC Chemical Group, Inc., Terre Haute, Ind.

[22] Filed: Aug. 4, 1975

[21] Appl. No.: 601,699

[52] U.S. Cl. ................ 260/307 F; 260/45.8 NZ
[51] Int. Cl.² ........................ C07D 261/08
[58] Field of Search ................. 260/307 FA

[56]   References Cited
       UNITED STATES PATENTS

| | | | |
|---|---|---|---|
| 2,448,890 | 9/1948 | Johnson | 260/307 F |
| 2,960,508 | 11/1960 | Croxall et al. | 260/307 |
| 3,558,615 | 1/1971 | Haynes et al. | 260/244 |

OTHER PUBLICATIONS

M. Senkus, J. Am. Chem. Soc., 67, 1515–1519 (1945).

*Primary Examiner*—Donald G. Daus
*Assistant Examiner*—Jose Tovar
*Attorney, Agent, or Firm*—Robert H. Dewey; Howard E. Post

[57] ABSTRACT

Vinyl oxazolidines corresponding to the formula

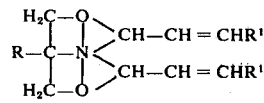

I or

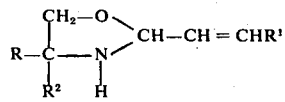

II wherein R is methyl, ethyl or hydroxymethyl, and $R^1$ is hydrogen, methyl or ethyl and $R^2$ is hydrogen, methyl or hydroxymethyl; or the oxazolidine can be the tris-oxazolidino derivative of 4-keto-9, 11, 13-octadectrienoic acid triglyceride(oiticica oil). The compounds have utility as dispersing agents in water-based paints.

12 Claims, No Drawings

VINYL OXAZOLIDINES

BACKGROUND OF THE INVENTION

This invention relates to vinyl oxazolidines. In a particular aspect this invention relates to polymerizable vinyl oxazolidines having utility as dispersing agents.

Powder coatings were developed as an alternative to solvent based coatings as a means of eliminating the volatile solvents from the environment. The development has been described by Emory P. Miller and David D. Taft in "Fundamentals of Powder Coatings", published by the Society of Mechanical Engineers, 20501 Ford Road, Dearborn, Mich., 1974. The coating is formulated as a dry powder consisting of one or more thermoplastic or thermosetting resin film-formers, or binders, and the necessary pigments to give the desired color. Sometimes a plasticizer for the film-former is included. These materials are finely comminuted and are applied to a metallic substrate by such methods as the fluidized bed process, electrostatic powder spraying, electrostatic fluidized bed and other electrostatic application methods.

Such coatings have been very successful but several problems have been encountered; also the equipment required to operate the various processes is very expensive. One of the most vexing problems is that of segregation of powders of different densities. It has been found that the ingredients must all have nearly equivalent densities to prevent segregation and subsequent non-homogeneous coating.

Another problem encountered is that of difficulty in controlling the film thickness. For example, when the powder is applied by electrostatic attraction, any inadequacies involved in applying the electrostatic charge will lead to uneven coating thickness. Also there is an inherently maximum film thickness which may prove inadequate for the anticipated use. Other problems involve those of occupational hygiene due to dust in air and the risk of explosion of the dusts. Accordingly an improved and less expensive process is needed to utilize these coatings to the best advantage.

It is known from U.S. Pat. Nos. 3,737,401 and 3,787,230 to apply these powder coatings, not only in dry form but also wet with a liquid which is not a solvent for the particles. These patents are incorporated herein by reference thereto. According to these patents, the powders are slurried in the liquid without use of a suspending or dispersant agent. Such slurries have many disadvantages, such as lack of stability. On the other hand, the use of any of the common dispersing agents weakens the film and renders it water sensitive because the dispersing agent remains in the film after baking but does not of itself contribute to the strength, durability and water resistance possessed by the film-formers. Also some of these dispersants migrate to the surface, giving it a greasy feel, and they also attract dirt, thus marring the appearance.

E. P. Hoffman and R. P. Sikorski in the U.S. Pat. No. 3,787,230 proposed as a solution to these problems to form a slurry of the powder paint in water using high speed agitation and optionally using a surfactant known as AEROSOL-T, a polypropylene base, non-water soluble powder. Although successful coatings are applied by this method, it suffers from the disadvantage that the slurries are not stable, i.e. the powder paint particles rapidly separate from the aqueous slurry, so best results are obtained only while continuously agitating the slurry during the coating process.

SUMMARY OF THE INVENTION

It is an object of this invention to provide novel vinyl oxazolidines.

It is another object of this invention to provide polymerizable vinyl oxazolidines.

It is still another object of this invention to provide stable water-dispersible coatings and thereby avoid expensive electrostatic application equipment.

It is still yet another object of this invention to provide water-dispersible coatings employing a dispersing agent wherein the dispersing agent is also a film-former.

Other objects of this invention will be apparent to those skilled in the art.

It is the discovery of the present invention to provide compounds represented by the formulas I or II:

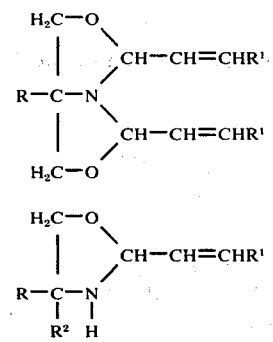

where R is methyl, ethyl or hydroxymethyl; $R^1$ is hydrogen or lower alkyl and $R^2$ is hydrogen, methyl or hydroxymethyl.

It is another embodiment of this invention to provide tris-oxazolidine derivatives of 4-keto-9,10,13-octadecatrienoic acid triglyceride. These compounds are excellent dispersing agents having particular utility in water-based coatings, especially coatings which are to be baked, e.g. water dispersions of powder coating. The dispersant of this invention is non-volatile and polymerizes during the baking step to form a component of the coating. The dispersant is non-migrating and does not come to the surface, as do other surfactants.

DETAILED DISCUSSION

It is the first embodiment of the present invention to provide dispersants and suspending agents for providing stable slurries of powder paints in water. These dispersants, which are believed to be novel, are represented by formulas I and II. Advantageously, these slurries may be prepared and stored for a considerable length of time with no significant separation of the powder paint.

The dispersants of the present invention are employed in an amount sufficient to provide the desired degree of stability of dispersion. Generally an amount of about 5–15%, preferably about 10% based on the weight of the powder paint, is sufficient. The amount of water employed is selected to provide the desired spraying characteristics. It is contemplated that suspensions of low water content will be prepared by the manufacturer and diluted by the user to fit his needs.

Generally a suspension wherein the water content comprises 40–60% by weight has a suitable spraying viscosity.

The compounds of the present invention are of the class of compounds generally designated as oxazolidines and bicyclic oxazolidines, or, more properly, 2,5,8 substituted 1-aza-3,7-dioxabicyclo-[3.3.0]-octanes.

These compounds can be readily prepared by the method of M. Senkus, *J. Am. Chem. Soc.* 67. 1515–1519 (1945), or William B. Johnson, U.S. Pat. No. 2,448,890, which are incorporated herein by reference thereto. Briefly, the compounds are prepared by reacting in an aqueous solution an aminoalkanediol compound represented by the formula

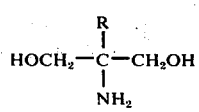   III or an amino alcohol represented by the formula

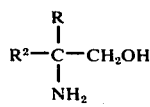   IV with a carbonyl compound represented by the formula $R^1CH=CHCHO$, V, where R, $R^1$ and $R^2$ have the same meanings defined above.

To form the bicyclic oxazolidine, the aldehyde is reacted with aminoalkanediol in about a 2:1 mole ratio. However when a 1:1 mole ratio is selected, the resulting compound corresponds to formula II wherein $R^2$ is hydroxymethyl. Such compounds are particularly preferred for the practice of this invention.

The mono-oxazolidine compounds of formula II where $R^2$ is hydrogen or methyl are similarly prepared by reacting the aldehyde with an amino-alcohol of formula IV, where R is methyl or ethyl, and $R^2$ is hydrogen or methyl, in about a 1:1 mole ratio.

In another embodiment of the present invention, the oxazolidine employed is obtained by reacting an aminoalcohol represented by formula IV with oiticica oil. The preferred compound is that prepared from 2-amino-2-methyl-1-propanol. Oiticica oil is known in the art and is commercially available. It is obtained from the seeds of hicania rigida. It is composed principally of the triglyceride of licanic acid (4-keto-α-elaeostearic acid, or, more precisely, 4-keto-9,11,13-octadecatrienoic acid) and a lesser amount of the triglyceride of elaeosteric acid. Although the latter compound does not form an oxazolidine, it polymerizes during the baking step and forms an integral part of the coating. Oiticica oil is described by T. P. Holditch and P. N. Williams in "The Chemical Constitution of Natural Fats", 4th Ed., John Wiley & Sons, Inc., New York, pp. 243–4, 253, 468–9 and 635.

It is yet another embodiment of the present invention to provide compositions consisting essentially of the powder paint dispersed in water using as the dispersing agent a bicyclic oxazolidine represented by the formula

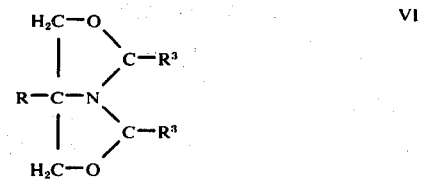   VI or

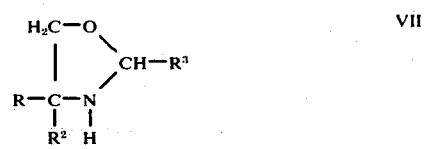   VII where R and $R^2$ have the same meaning as defined hereinbefore and $R^3$ is an alkyl group of from 3 to 6 carbon atoms. These compounds are prepared by reacting an aminoalkanediol represented by formula III or an alkanolamine represented by formula IV with an aldehyde having from 4 to 7 carbon atoms by methods known in the art, as previously set forth. The powder paint can be any of those known in the art as set forth hereinbefore. There is no limitation as to the type of powder paint that can be suspended.

Although the oxazolidines represented by formulas VI and VII are saturated, they apparently are either volatilized during the heating step or become an integral part of the coating by chemical reaction or other. In any case, they contribute none of the deleterious effects previously observed from surfactants remaining in the coating.

It is still yet another embodiment of the present invention to provide compositions consisting essentially of the powder paint dispersed in water using as the dispersing agent an oxazoline represented by the formula

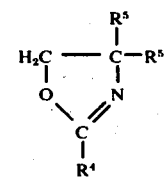

where $R^4$ is an alkyl group of 1 to 3 carbon atoms and $R^5$ is hydrogen, methyl or hydroxylmethyl. These compounds are known in the art, e.g. from R. F. Purcell, U.S. Pat. No. 3,248,397. They are easily prepared by reacting a carboxylic acid represented by the formula $R^4COOH$ with an alkanolamine of formula IV or an aminoalkanediol of formula III.

Such compositions generally contain from about 1–2% to about 7% or more of oxazoline, from about 40% to about 97% of powder paint, and from zero to about 55% of water. The invention contemplates a water-free composition containing 3–7% of oxazoline and 93–97% of powder paint which can be mixed with water just before use. The amount of water employed would be an amount to provide a suitable viscosity for application; usually an amount sufficient to provide a mixture containing from about 30% to about 55% water is adequate for most applications methods such as brushing, dipping or spraying.

The resins used in the practice of this invention are fusible thermosetting and thermoplastic resins. The resins used include but are not limited to polyvinyl chloride, ethylenevinyl chloride copolymers and vinyl acetate-chloride copolymers, including those modified by one or more additives, e.g. maleic anhydride; esters of cellulose such as cellulose acetate, cellulose acetate-butyrate, cellulose propionate, and cellulose butyrate; polypropylene; the polyamides such as nylon 6, nylon 11, and nylon 12; polyesters such as those obtained by esterifying mixtures of polybasic organic acids and polyols, especially the high molecular weight polyethylene terephthalates or isophthalates; the epoxy resins such as the diglycidyl ethers of bisphenol A, the novolac epoxy resin, or the cycloaliphatic epoxy resins formed by the reaction of cyclic olefins with peracetic acid, and curing agents therefore, such as aliphatic or aromatic amines, acid anhydrides and boron trifluoride; acrylics such as the lower aliphatic acrylic and methacrylic esters and amides.

Any of the powder coatings of the prior art can be used in the practice of this invention because they can be easily dispersed with the vinyl oxazolidines without regard to the resin involved. The coated substrate is then heated to a temperature sufficient to fuse the powdered coating, then cooled.

The invention will be better understood by reference to the following examples. It is understood, however, that the examples are intended only to illustrate the invention and are not intended to be limiting.

EXAMPLE 1

2-Amino-2-ethyl-1,3-propanediol (AEPD), 240 g (2 moles) was dissolved in 275 g of distilled water. Dibutyl hydrogen phosphate, 2 g, and triethyl phosphite (0.2 g) were added and the solution was chilled in an ice bath. Acrolein, 110 g (1.97 moles containing 0.1% hydroquinone as a polymerization inhibitor was added dropwise over a 30 min. period with constant agitation. The agitation was continued for another 15 min. at which time the reaction was adjudged to be complete. The solution contained 50±% water.

A commercial, clear powder, 19 g, intended for electrostatic spray (the powder used was an epoxy phenolic No. 464-84A marketed by Schenectady Chemicals, Inc., Schenectady, N.Y.) was mixed with 1 g of the vinyl oxazolidine solution obtained above and 10 g of distilled water were added. The mixture was stirred until the powder was completely wetted. Then additional water was added to produce the desired viscosity; pumpable slurry was obtained with 8 g, a smooth latex with 12 g, and a sprayable paint with 15 g of water.

The suspension was applied as a spray to a steel panel. The panel was baked for 15 min. in a 400° F oven, then quenched by immersing in cool water.

The suspension provided a hard, smooth coating 1.2 ml thickness having a high gloss. It could withstand an impact of 160 in./lb., both direct and reverse.

EXAMPLE 2

The experiment of Example 1 was repeated in all essential details except that a pigmented, white epoxy powder was substituted for the clear one. The powder used was identified as 484-106, marketed by Schenectady Chemicals, Inc. A hard, glossy film was obtained which could withstand an impact of more than 160 in./lb. both direct and reverse.

EXAMPLE 3

The experiment of Example 1 was repeated in all essential details except that 2-amino-2-methyl-1-propanol was substituted for AEPD on a 0.5:1 mole basis. There was obtained a compound represented by formula II wherein R and $R^2$ are methyl and $R^1$ is hydrogen (the compound may have been in equilibrium with its Schiff's base isomer). The product was an effective dispersant for a powder coating.

EXAMPLE 4

The experiment of Example 3 was repeated in all essential details that crotonaldehyde was substituted for acrolein on an equi-molar basis. The product was an effective dispersant for a powder coating.

EXAMPLE 5

The experiment of Example 3 was repeated in all essential details except that oiticica oil was substituted for acrolein on an equi-molar basis. The product was an effective dispersant for a powder coating.

EXAMPLE 6

The experiment of Example 3 was repeated in all essential details except that tris(hydroxymethyl)aminomethane, 160 g (1.32 moles) was substituted for AEPD. It was slurried in 191 g of water and was reacted with acrolein, 71 g (1.27 moles), maintaining the reaction mixture under a nitrogen blanket and at a temperature of 15°–40° C. Agitation was continued for 30 min. after all the acrolein had been added. The resultant product was clear, odorless and had a viscosity of less than A (Gardner scale), a color (Gardner scale) of less than 8. It had a non-volatile content of 50%.

The product was an effective dispersant for a powder coating. The dispersion was applied to steel panels and baked, forming a hard, durable coating.

EXAMPLE 7

2-Amino-2-ethyl-1,3-propanediol, 200 lb. (1.68 moles) was transfered to a reaction vessel and 125 lb. of propionic acid (1.69 moles) was added thereto with agitation under a nitrogen blanket. The mixture was heated slowly to about 200° removing water of reaction, about 60 lb. Heating was maintained until the acid value was less than 2 whereupon the mixture was allowed to cool. The resulting compound was clear and had a viscosity less than A (Gardner scale); a color less than 12 (Gardner scale); and an acid value less than 2.

The product was an effective dispersant for a powder coating. The dispersion was applied to steel panels and baked, forming a hard, durable coating.

EXAMPLE 8

The experiment of Example 1 was repeated in all essential details except that oiticica oil was substituted for acrolein on a ketone-equivalent basis and 2-amino-2-methyl-1-propanol was substituted for AEPD.

The product was used as a dispersing agent for suspending a powder paint, commercially identified as Dri-Dex Gray, in water in the following proportions:

| | |
|---|---|
| Dispersing agent | 2 parts |
| Powder paint | 18 |

| | |
|---|---|
| Water | 20 |

The resulting suspension was a loose, thixotropic gel which sprayed well onto a steel panel. The film after baking was fully satisfactory.

I claim:

1. An oxazolidine represented by the formula

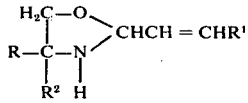

wherein R is hydroxymethyl, $R^2$ is hydrogen, methyl or hydroxymethyl and $R^1$ is hydrogen, methyl or ethyl.

2. The oxazolidine of claim 1 wherein $R^2$ is hydroxymethyl.

3. The oxazolidine of claim 1 wherein $R^2$ is hydrogen.
4. The oxazolidine of claim 1 wherein $R^1$ is hydrogen.
5. The oxazolidine of claim 1 wherein $R^1$ is methyl.
6. The oxazolidine of claim 1 wherein $R^1$ is ethyl.
7. An oxazolidine represented by the formula

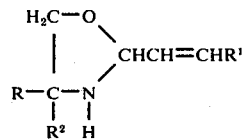

wherein $R^2$ is hydroxymethyl, R is methyl, ethyl or hydroxymethyl and $R^1$ is hydrogen, methyl or ethyl.

8. The oxazolidine of claim 7 wherein R is methyl.
9. The oxazolidine of claim 7 wherein R is ethyl.
10. The oxazolidine of claim 7 wherein $R^1$ is hydrogen.
11. The oxazolidine of claim 7 wherein $R^1$ is methyl.
12. The oxazolidine of claim 7 wherein $R^1$ is ethyl.

* * * * *

UNITED STATES PATENT OFFICE
CERTIFICATE OF CORRECTION

Patent No. 3,994,919            Dated November 30, 1976

Inventor(s) Louis A. Jurisch

It is certified that error appears in the above-identified patent and that said Letters Patent are hereby corrected as shown below:

In the Abstract, Formula I 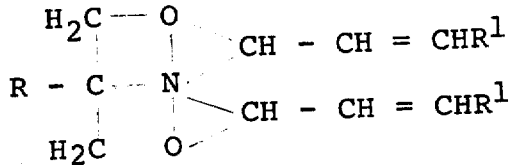

should read 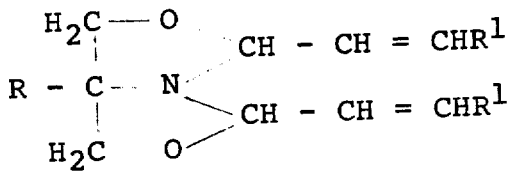

Signed and Sealed this

*twelfth* Day of *July 1977*

[SEAL]

Attest:

RUTH C. MASON
*Attesting Officer*

C. MARSHALL DANN
*Commissioner of Patents and Trademarks*